(12) United States Patent
Manginell et al.

(10) Patent No.: US 6,171,378 B1
(45) Date of Patent: Jan. 9, 2001

(54) CHEMICAL PRECONCENTRATOR

(75) Inventors: Ronald P. Manginell, Albuquerque; Gregory C. Frye-Mason, Cedar Crest, both of NM (US)

(73) Assignee: Sandia Corporation, Albuquerque, NM (US)

(*) Notice: Under 35 U.S.C. 154(b), the term of this patent shall be extended for 0 days.

(21) Appl. No.: 09/369,664

(22) Filed: Aug. 5, 1999

(51) Int. Cl.⁷ .................................................. B01D 53/04
(52) U.S. Cl. .......................... 96/143; 55/DIG. 5; 96/101; 96/154
(58) Field of Search .................................. 95/82, 87, 89, 95/90, 116, 148; 96/4, 11, 101, 102, 105, 126, 143, 146, 154; 55/524, DIG. 5

(56) References Cited

U.S. PATENT DOCUMENTS

| | | | |
|---|---|---|---|
| 4,433,982 | * | 2/1984 | Odensheimer et al. ............... 96/4 |
| 4,599,095 | * | 7/1986 | Barnes et al. ........................ 96/146 |
| 5,087,275 | * | 2/1992 | Pribat et al. ......................... 96/101 |
| 5,151,110 | * | 9/1992 | Bein et al. ........................ 96/101 X |
| 5,224,972 | | 7/1993 | Frye ..................................... 55/18 |
| 5,501,893 | | 3/1996 | Laermer ............................ 428/161 |
| 5,589,396 | | 12/1996 | Frye ..................................... 436/73 |
| 5,720,798 | * | 2/1998 | Nickerson et al. ................. 96/102 |
| 5,770,275 | | 6/1998 | Raman ................................ 427/535 |
| 5,939,614 | * | 8/1999 | Walters et al. .................... 95/82 X |

OTHER PUBLICATIONS

S.C. Terry, J.H. Jerman and J.B. Angell, "A Gas Chromatographic Air Analyzer Fabricated on a Silicon Wafer," *IEEE Transactions on Electron Devices*, vol. ED–26, pp. 1881–1886, Dec. 1979.

M.S. Nieuwenhuizen and A. Venema, "Surface Acoustic Wave Chemical Sensors," *Sensors and Materials*, vol. 5, pp. 261–300, 1989.

G.C. Frye, C.J. Brinker, T. Bein, C.S. Ashley and S.L. Martinez, "Controlled Microstructure Oxide Coatings for Chemical Sensors," *Proceedings of the 1990 Solid State Sensors and Actuators Workshop*, pp. 61–64 (IEEE, New York, 1990).

C. Mastrangelo and R.S. Muller, "Microfabricated Thermal Absolute–Pressure Sensor with On–Chip Digital Front–End Processor", *IEEE Journal of Solid–State Circuits*, vol. 26, pp. 1998–2007, Dec. 1991.

J.W. Bosman, J.M. DeBruijn, F.R. Riedijk, B.W. Oudheusden and J.H. Huijsing, "Integrated Smart Two–Dimensional Thermal Flow Sensor with Seebeck–Voltage–to–Frequency Conversion," *Sensors and Actuators A*, vol. 31, pp. 9–16, 1992.

(List continued on next page.)

*Primary Examiner*—Robert H. Spitzer
(74) *Attorney, Agent, or Firm*—John P. Hohimer

(57) ABSTRACT

A chemical preconcentrator is disclosed with applications to chemical sensing and analysis. The preconcentrator can be formed by depositing a resistive heating element (e.g. platinum) over a membrane (e.g. silicon nitride) suspended above a substrate. A coating of a sorptive material (e.g. a microporous hydrophobic sol-gel coating or a polymer coating) is formed on the suspended membrane proximate to the heating element to selective sorb one or more chemical species of interest over a time period, thereby concentrating the chemical species in the sorptive material. Upon heating the sorptive material with the resistive heating element, the sorbed chemical species are released for detection and analysis in a relatively high concentration and over a relatively short time period. The sorptive material can be made to selectively sorb particular chemical species of interest while not substantially sorbing other chemical species not of interest. The present invention has applications for use in forming high-sensitivity, rapid-response miniaturized chemical analysis systems (e.g. a "chem lab on a chip").

38 Claims, 12 Drawing Sheets

Section 1 - 1

OTHER PUBLICATIONS

R.E. Cavicchi, J.S. Suehle, P. Chaparala, K.G. Kreider, M. Gaitan and S. Semancik, "Micro–Hotplate Gas Sensor," *Proceedings of the Solid–State and Actuator Workshop*, Hilton Head, SC, Jun. 13–16, 1994, pp. 53–56.

M. Zanini et al., Fabrication and Properties of a Si–Based High Sensitivity Microcalorimetric Gas Sensor, *Proceedings of the Solid–State and Actuator Workshop*, Hilton Head, SC, Jun. 13–16, 1994, pp. 176–179.

G.T.A. Kovacs. C.W. Storment and S.P. Kounaves, "Microfabricated Heavy Metal Ion Sensor," *Sensors and Actuators B*, vol. 23, pp. 41–47, 1995.

C.G. Neubold, J. Wang, X. Cai and K. Kalcher, "Screen–Printed Electrodes for Nitrite Based on Anion–Exchanger–Doped Carbon Inks," *Analyst*, vol. 120, pp. 2377–2380, 1995.

J.Wang, G. Rivas, X Cai, H. Shiraishi, P.A.M. Farias, N. Dontha and D. Luo, "Accumulation and Trace Measurements of Phenothiazine Drugs at DNA–Modified Electrodes," *Analytica Chimica Acta*, vol. 332, pp. 139–144, 1996.

E.H. Klaassen and G.T.A. Kovacs, "Integrated Thermal Conductivity Vacuum Sensor," *Proceedings of the Solid–State and Actuator Workshop*, Hilton Head, SC, Jun. 4–6, 1996, pp. 249–252.

B.C.S. Chou, Y.–M. Chen, M. Ou–Yang, J.–S. Shie, "A Sensitive Pirani Vacumm Sensor and the Electrothermal SPICE Modelling," *Sensors and Actuators A*, vol. 53, pp. 273–277, 1996.

L. Qiu, S. Hein, E. Obermeier and A. Schubert, "Micro Gas–Flow Sensor with Integrated Heat Sink and Flow Guide," *Sensors and Actuators A*, vol. 54, pp. 5437–5441, 1996.

N.K. Raman, M.T. Anderson and C.J. Brinker, "Template–Based Approaches to the Preparation of Amorphous Nanoporous Silicas," *Chemistry of Materials*, vol. 8, pp. 1682–1701, 1996.

R.P. Manginell, J.H. Smith and A.J. Ricco, "An Overview of Micromachined Platforms for Thermal Sensing and Gas Detection," *Proceedings of the 4th Annual Symposium on Smart Structures and Materials*, SPIE vol. 3046, pp. 273–284 (SPIE, Bellingham, WA, 1997).

S.L. Firebaugh, K.F. Jensen and M.A. Schmidt, "Investigation of High–Temperature Degradation of Platinum Thin Films with an *In Situ* Resistance Measurement Apparatus," *Journal of Microelectromechanical Systems*, vol. 7, pp. 128–135, Mar. 1998.

S.J. Martin, M.A. Butler, J.J. Spates, M.A. Mitchell and W.K. Schubert, "Flesural Plate Wave Resonator Excited with Lorentz Forces," *Journal of Applied Physics*, vol. 83, pp. 4589–4601, May 1, 1998.

R.P. Manginell, G.C. Frye–Mason, W.K. Schubert, R.J. Shul and C.G. Willison, "Microfabrication of Membrane–Based Devices by HARSE and Combined HARSE/Wet Etching," *Proceedings of the SPIE Conference on Micromachining and Microfabrication Process Technology IV*, SPIE vol. 3511, pp. 269–276, Sep. 1998.

Y. Lu, G. Cao, R.P. Kale, S. Prabakar, G.P. Lopez and C.J. Brinker, "Microporous Silica Prepared by Organic Templating: Relationship Between the Molecular Template and Pore Structure," *Chemitry of Materials*, vol. 11, pp. 1223–1229, 1999.

* cited by examiner

CHEMICAL PRECONCENTRATOR

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates generally to chemical analysis (e.g. by gas chromatography), and in particular to a compact chemical preconcentrator formed on a substrate with a heatable sorptive membrane that can be used to accumulate and concentrate one or more chemical species of interest over time and then rapidly release the concentrated chemical species upon demand for chemical analysis.

BACKGROUND OF THE INVENTION

Presently, there is a need for autonomous, portable, hand-held chemical analysis systems for the rapid and sensitive detection of particular chemicals including pollutants, high explosives and chemical warfare agents. Such miniaturized chemical analysis systems, which have been termed "chemical laboratories on a chip", are currently being developed based on gas chromatography. The requirements for these chemical analysis systems are that they provide a high chemical selectivity to discriminate against potential background interferents which may be present at up to a thousand-fold or more higher concentration, that the chemical analysis be performed on a short time scale (e.g. in a minute or less) and that the chemical analysis be performed with high sensitivity (e.g. at concentrations down to the part-per-billion level). Low electrical power consumption is also needed for field use over a prolonged time period.

The present invention is of a millimeter-sized chemical preconcentrator which can be used with the above miniaturized chemical analysis systems to increase the sensitivity and selectivity with which chemical analysis measurements can be made.

An advantage of the chemical preconcentrator of the present invention is that it can be integrated with other elements of a chemical analysis system in a hybrid or monolithic fashion to provide a substantial improvement in the detectivity of particular chemical species of interest.

A further advantage of the present invention is that a sorptive coating of the chemical preconcentrator can be tailored for chemical selectivity to one or more chemical species of interest and thereby accumulate and concentrate these chemical species from an ambient or sample vapor over time while being relatively insensitive to other chemical species not of interest.

Yet another advantage of the present invention is that the accumulated chemical species of interest can be concentrated in a small area and subsequently released suddenly by thermal desorption to form a sample plug having a narrow temporal width and a relatively high concentration of the chemical species of interest, thereby improving the detectability of each chemical species of interest using the chemical analysis system.

Still another advantage of the chemical preconcentrator of the present invention is that it has a very small heat capacity to allow rapid heating and release of the concentrated chemical species of interest on a time scale of a fraction of a second.

A further advantage of the chemical preconcentrator of the present invention is that it is applicable to different types of chemical analysis systems, including systems based on gas chromatography and systems based on mass spectrometry.

These and other advantages of the present invention will become evident to those skilled in the art.

SUMMARY OF THE INVENTION

The present invention relates to a chemical preconcentrator apparatus (also termed herein a chemical preconcentrator), comprising a substrate having a suspended membrane formed thereon; a resistive heating element disposed on a surface of the membrane; and a sorptive material disposed on at least one surface of the membrane to sorb and concentrate at least one chemical species of interest from a vapor (e.g. a gaseous ambient) over time, with the chemical species being releasable from the sorptive material upon heating of the sorptive material by the resistive heating element. Various types of sorptive materials including microporous materials, sol-gel oxides and polymers can be used in the chemical preconcentrator apparatus, with a particular sorptive material being selected to sorb particular chemical species of interest. Additionally, a chemical modification of the surface of the sorptive material (e.g. a sol-gel oxide) can be used to further enhance sorption of the chemical species of interest.

The substrate used to form the chemical preconcentrator apparatus generally comprises a semiconductor (e.g. silicon or gallium arsenide) or a dielectric (e.g. a glass, crystalline quartz, fused silica, a plastic, a resin or a ceramic). The membrane preferably comprises silicon nitride, although other materials such as polycrystalline silicon, silicon oxynitride and silicon carbide can also be used to form the membrane. The resistive heating element formed on the membrane generally comprises a circuitous metal trace formed from one or more layers of deposited metals including platinum, molybdenum, titanium, chromium, palladium, gold and tungsten. To provide a more uniform heating of the sorptive material, an optional heat-spreading layer (e.g. comprising aluminum or silicon) can be disposed over the resistive heating element. Finally, an optional temperature sensor can be located on the membrane proximate to the resistive heating element to aid in controlling and measuring the temperature during heating of the membrane, with the temperature sensor generally comprising a circuitous metal trace (and in some instances being the resistive heating element itself) which forms a resistive temperature sensor or a thermocouple.

The present invention also relates to a method for forming a chemical preconcentrator apparatus for sorbing a chemical species of interest from a vapor over time and releasing the chemical species of interest upon demand. The method comprises steps for forming a suspended membrane on a substrate; forming a resistive heating element on a surface of the suspended membrane; and coating at least one surface of the suspended membrane with a sorptive material capable of sorbing the chemical species of interest. The step for forming the suspended membrane comprises depositing a film over a top surface of the substrate, and removing material from the substrate underneath a portion of the deposited film. This can be done in different ways depending upon particular embodiments of the present invention. A first method to remove material underneath the membrane comprises one or more etching steps for etching the substrate from its bottom surface. This can be done using either anisotropic wet etching (e.g. with potassium hydroxide) or by reactive ion etching, or by a combination of both types of etching.

A preferred method for etching through the substrate from its bottom surface (i.e. from a backside of the substrate) is to etch through the substrate using an anisotropic dry etching process (e.g. reactive ion etching). This produces an etch opening with substantially vertical sidewalls, thereby minimizing the size of the opening and conserving space on the substrate. In some cases, an additional anisotropic wet etching step may be required to completely remove the substrate material underneath the membrane. Alternately, the substrate can be etched entirely with an anisotropic wet etching process in which case a plurality of angled sidewalls can be formed in etching through the substrate.

Another method for etching through the substrate which is based on surface micromachining process steps is to deposit a sacrificial layer over the substrate, and then deposit a film over the sacrificial layer. A plurality of openings can be formed through the film to expose the sacrificial layer so that the sacrificial layer can be removed, at least in part, through the openings formed in the film (e.g. by etching away the sacrificial layer using a wet etchant comprising hydrofluoric acid, or by dissolving the sacrificial layer in a solvent such as acetone). When this method is used, the film can comprise silicon nitride, silicon (e.g. polycrystalline silicon), silicon oxynitride or silicon carbide. Additionally, the sacrificial layer can comprise silicon dioxide, a silicate glass, a resin or a polymer (including a photoresist).

The step for forming the resistive heating element comprises depositing one or more metal layers (e.g. comprising platinum, molybdenum, titanium, chromium, palladium, gold or tungsten) and patterning the metal layers to form a circuitous metal trace. Once the circuitous metal trace for the heating element has been formed, it can be annealed to relieve any stress in the metal trace. The step of forming the resistive heating element is preferably performed after depositing the membrane film over the substrate and before removing the substrate material to form the suspended membrane. This allows the resistive heating element to be encapsulated in an etch-resistant material (e.g. a photoresist) during the step for etching the substrate and removing the substrate material from underneath the deposited membrane film.

The surface of the suspended membrane (and the overlying resistive heating element) can then be coated with a sorptive material such as a polymer, a microporous material or a sol-gel oxide. When the sorptive material is coated as a liquid, it can be dried and cured by heating. In some instances, this can be done by applying electrical power to the resistive heating element.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings:

FIG. 1b shows a schematic cross-section view of the chemical preconcentrator apparatus along the lines 1—1 in FIG. 1a.

DETAILED DESCRIPTION OF THE INVENTION

Figure 1A:
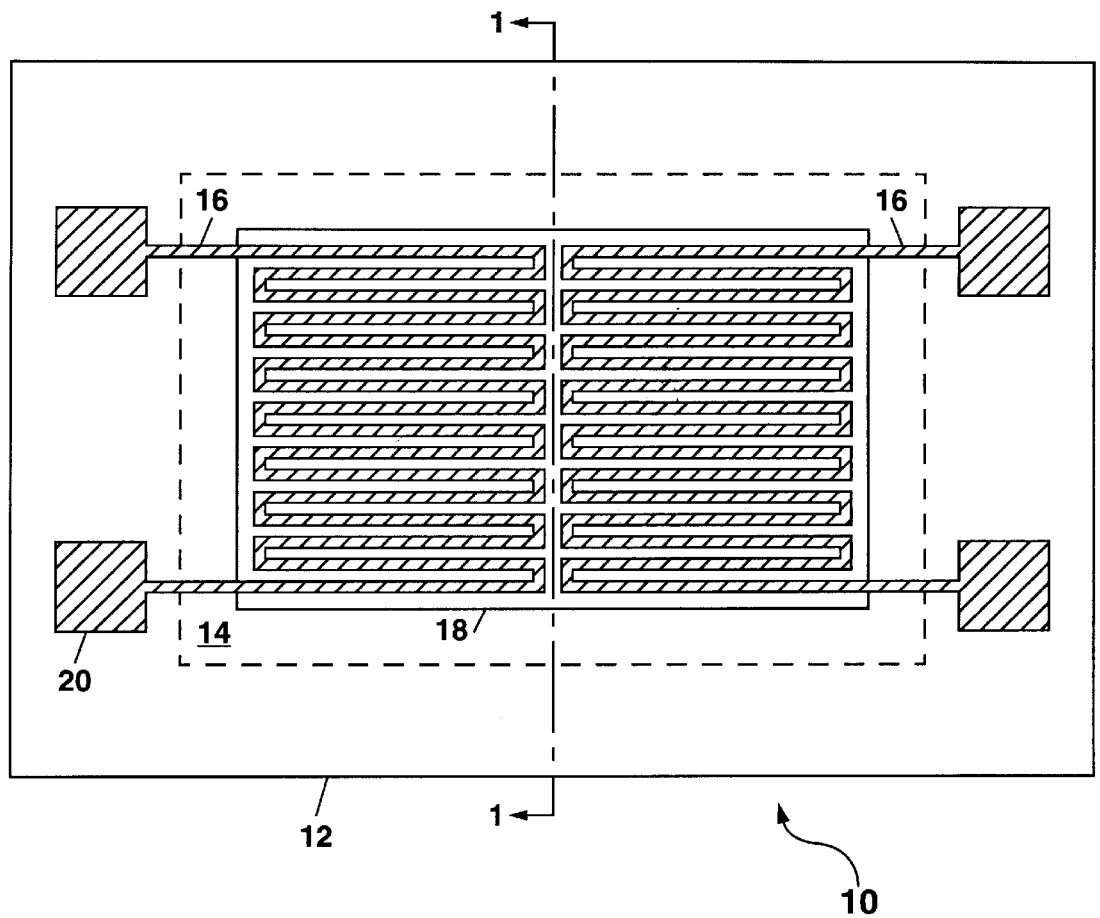
FIG. 1a shows a schematic plan view of an example of the chemical preconcentrator apparatus of the present invention.
Figure 1B:
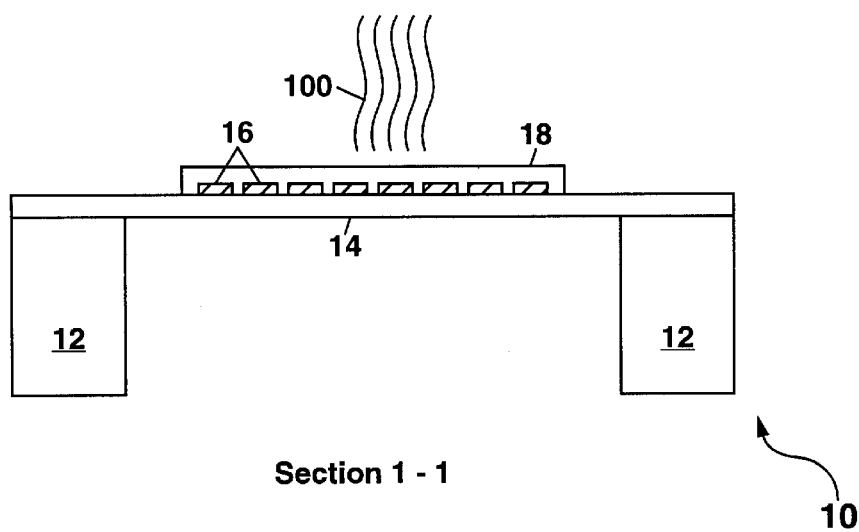

Referring to FIGS. 1a and 1b, there is shown schematically a plan view and a cross-section view, respectively, of an example of a chemical preconcentrator apparatus 10 formed according to the present invention. In FIGS. 1a and 1b, the chemical preconcentrator 10 comprises a substrate 12 having a suspended membrane 14 formed thereon. One or more resistive heating elements 16 and a coating or layer of sorptive material 18 are formed on the membrane 14. The sorptive material 18 acts to sorb and concentrate one or more chemical species of interest from an ambient or a sample vapor 100 over time and can suddenly release the chemical species in concentrated form upon rapid heating of the sorptive material 18 using the heating elements 16. The terms "sorb" and "sorptive" as used herein are defined to include both absorption and adsorption of the chemical species of interest.

The substrate 12 in the example of FIGS. 1a and 1b comprises monocrystalline silicon, with a thickness of generally about 400–500 $\mu$m. In other embodiments of the present invention, the substrate 12 can be a semiconductor (e.g. gallium arsenide) or a dielectric material (e.g. a glass, crystalline quartz, fused silica, a plastic, a resin or a ceramic).

In FIGS. 1a and 1b, the suspended membrane 14 is typically formed as a rectangle or polygon with lateral dimensions from about one to a few millimeters on a side (e.g. a square of 1–3 mm on a side), or alternately as a circle or ellipse with a size from one to a few millimeters. The suspended membrane 14 is supported at its edges by attachment to the substrate 12 (e.g. by adhesion of a deposited membrane-forming layer to the substrate 12 or to a sacrificial layer overlying the substrate 12). The suspended membrane 14 can be formed, for example, by depositing a film of material (e.g. silicon nitride) over the substrate 12 and subsequently removing a portion of the substrate 12 using one of the methods to be described hereinafter. The membrane 14 is sufficiently thick (generally about 0.5–1 μm total thickness) for robustness as required for handling and to support the heating element 16 and a layer of the sorptive material 18 which can be several microns thick. Additionally, the membrane 14 must be sufficiently robust to withstand any stress induced by a mismatch in thermal expansion coefficients of the membrane 14 and the supporting substrate 12 upon heating to a temperature of up to several hundred ° C.

Low-pressure chemically vapor deposited (LPCVD) silicon nitride is a preferred membrane material due to its low stress, low thermal conductivity and compatibility with integrated circuit (IC) processing steps. The low thermal conductivity of a silicon nitride membrane 14 minimizes heat loss by conduction from a central portion of the membrane 14 heated by the resistive heating element 16 outward to the supporting substrate 12. The silicon nitride membrane 14 also has a low heat capacity which allows it to be rapidly heated to a temperature of several hundred ° C. (e.g. 200–400° C.) on a time scale of a few milliseconds (e.g. 6–15 ms) using a low electrical heating power (e.g. 50–250 mW).

In the example of FIGS. 1a and 1b, each resistive heating element 16 is formed by depositing one or more layers of a metal over the membrane 14 and patterning the layers of metal to form a circuitous metal trace which generally has a serpentine or boustrophendon shape. Other arrangements of the resistive heating element(s) 16 are possible. The resistive heating elements 16 in FIG. 1a, which generally cover about 50% of the area of the suspended membrane 14, are thermally isolated from the substrate 12 by their placement on the suspended membrane 14. This thermal isolation on a low-heat-capacity suspended membrane 14 provides for rapid heating with a relatively low electrical input power.

The two resistive heating elements 16 in the example of the present invention in FIGS. 1a and 1b can be electrically connected in series or in parallel to a power source for operation, with the two heating elements 16 generally being operated simultaneously to release a sorbed chemical species of interest for analysis. Parallel operation allows the use of a lower operating voltage to drive the resistive heating elements 16. However, in some embodiments of the present invention a sequential operation of the two resistive heating elements 16 can be used. This can be done, for example, to allow two separate analyses of the chemical species of interest. Alternately, each resistive heating element can be used to heat a different sorptive material 18, with each sorptive material being tailored to selectively sorb different chemical species of interest. In other embodiments of the present invention, a single resistive heating element 16 can be used.

The metal layers forming the heating element 16 can include an adhesion layer (e.g. titanium or chromium), and a resistive layer (e.g. platinum, molybdenum or tungsten). To facilitate temperature measurement or control, it is desirable for the resistive layer to have a suitably high temperature coefficient of resistance (TCR) on the order of 2500–3000 ppm/° C. The term "metal " as used herein is intended to include elemental metals and metal alloys. Platinum is particularly well suited for use as the resistive layer since it is chemically inert to many chemical species of interest. If the metals forming the resistive heating element 16 are susceptible to degradation due to evaporation or to attack due to a harsh chemical environment in which the chemical preconcentrator 10 is to be used, the resistive heating element 16 can be protected by a thin (e.g. 0.2–0.3 μm) overlayer such as silicon nitride or silicon carbide which can be deposited by a plasma-enhanced chemical vapor deposition (PECVD) process. In other embodiments of the present invention, the resistive heating element 16 can be formed of other types of electrically-conductive materials (e.g. electrically-conducting polymers, or indium-tin-oxide).

The various metals used to form the resistive heating element 16 can be deposited by evaporation or sputtering and patterned using a photolithographically defined mask and lift-off. Alternately wet chemical etching can be used to pattern the metals using an etchant that is specific to the particular metals used. The adhesion layer can be, for example, 10–20 nanometers thick; and the resistive layer can be, for example, 100–200 nanometers thick. A diffusion barrier (e.g. comprising palladium) can optionally be used in forming the resistive heating element 16.

As shown in FIG. 1a, the resistive heating element 16 can further include a plurality of bond pads 20 which can be formed, for example, of a 15-nanometer-thick layer of titanium and a 100-nanometer-thick overlayer of gold. Furthermore, to improve the heating uniformity and reduce thermal gradients of the membrane 14 during heating, a thin heat-spreading layer (e.g. 0.5 μm) of polycrystalline silicon or a metal such as aluminum or gold can optionally be deposited above the resistive heating element 16 and electrically insulated therefrom (e.g. by a thin silicon nitride layer).

The resistive heating element 16 is preferably formed over a deposited film from which the suspended membrane 14 is formed prior to the removal of a portion of the substrate 12 at the location wherein the suspended membrane 14 is to be formed. Once the resistive heating element 16 is formed, it can be covered with a protection layer (e.g. photoresist) during subsequent processing required to remove the substrate material underneath the membrane 14. The protection layer serves to protect the membrane 14 and heating element 16 from exposure to the etchant used to remove the substrate material.

Various methods exist to remove the substrate material and thereby form the suspended membrane 14. These methods will be described hereinafter with reference to FIGS. 2a–2h, 3a–3e, and 4a–4f.

In FIGS. 2a–2h, the chemical preconcentrator 10 can be formed by etching a silicon substrate 12 using an anisotropic wet etchant such as potassium hydroxide (KOH), tetramethyl ammonium hydroxide (TMAH), ethylenediamine pyrocatechol (EDP) or the like. These anisotropic wet etchants etch silicon with the etching terminating at (111) crystallographic planes. For a (100)-oriented silicon substrate 12, this can result in an etched cavity having sloping sidewalls at an angle of about 55°. Other anisotropic wet etchants are known to the art for other types of substrates 12 comprising semiconductors (e.g. gallium arsenide) or dielectric materials (e.g. crystalline quartz).

In each of the various methods for forming the chemical preconcentrator 10 of the present invention, a number of processing steps are required including processes such as material deposition, photolithography, masking, etching, mask stripping and cleaning which are well-known in the semiconductor integrated circuit (IC) industry. Therefore, only a limited number of relevant processing steps will be described herein in detail. Additionally, it will be understood by those skilled in the art that the term "patterning" as used herein refers to a sequence of well-known IC processing steps including applying a photoresist to the substrate 12, prebaking the photoresist, aligning the substrate 12 with a photomask, exposing the photoresist through the photomask, developing the photoresist, baking the photoresist, etching away the surfaces not protected by the photoresist, and stripping the protected areas of the photoresist so that further processing can take place.

Figure 2A:
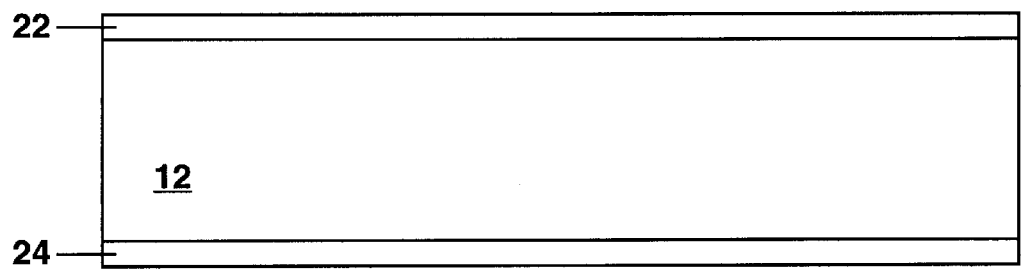
FIGS. 2a–2h show schematic cross-section views to illustrate a first method for forming the chemical preconcentrator.

In FIG. 2a, a (100) silicon substrate 12 polished on its top and bottom surfaces can be initially prepared by forming a thermal oxide (not shown) on each surface of the substrate 12. The substrate can then be coated on both sides with a 0.5–1 $\mu$m film of silicon nitride using low-pressure chemical vapor deposition (LPCVD). This forms an upper silicon nitride layer 22 which will be used to form the suspended membrane 14 and a lower silicon nitride layer 24 which will be used to form an etch mask for defining the material to be removed from the substrate 12 underneath the membrane 14.

Figure 2B:
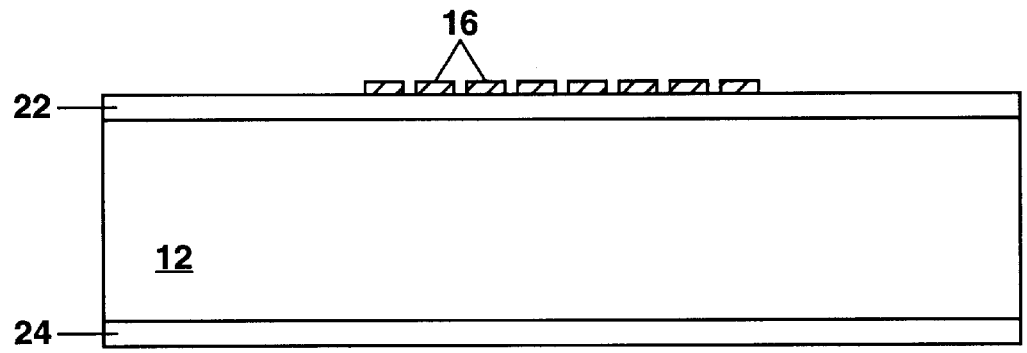

In FIG. 2b, the resistive heating element 16 can be formed by depositing and patterning one or more layers of metal on the upper silicon nitride layer. To form a platinum heating element 16, a 15-nm-thick layer of titanium can be deposited on the upper silicon nitride layer 22 through a patterned photoresist mask having a circuitous (i.e. meandering) opening therethrough, followed by deposition of a 100-nm-thick layer of platinum. Lift-off of the photoresist mask can then be used to pattern the circuitous metal trace of the heating element 16. The circuitous metal trace can then be annealed at 500° C. in a nitrogen gas ($N_2$) ambient for one-half hour to relieve any stress in the trace resulting from deposition and lift-off. Bond pads 20 can be formed at the ends of the circuitous metal trace by depositing a 15-nm-thick layer of titanium and a 100-nm-thick layer of gold through another patterned photoresist mask and again using lift-off. The resistance and operating voltage of the heating element 16 will depend upon the particular metal(s) used and the layer thickness of the metal(s), and also on the temperature to which the element 16 is heated. Typical operating voltages are in the range of 5–20 volts.

Figure 2C:
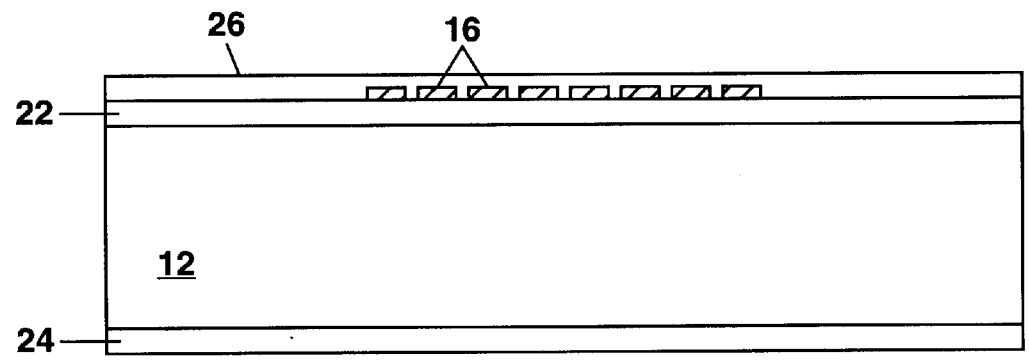
Figure 2D:
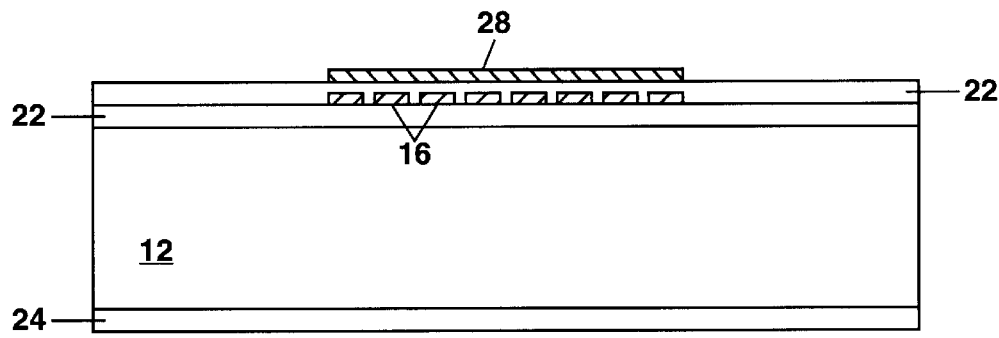

In FIG. 2c, an overlayer 26 of silicon nitride can be deposited by LPCVD to blanket the substrate 12 and the resistive heating element 16. This overlayer 26, which can be about 100–200 nanometers thick, serves to electrically insulate the heating element 16 from a heat-spreading layer 28 which is subsequently deposited and patterned to overlie the resistive heating element 16 and improve heating uniformity. The heat-spreading layer 28, which is shown in FIG. 2d, can comprise, for example, about 200 nanometers of aluminum, gold or polycrystalline silicon. In other embodiments of the present invention, the heat-spreading layer 28 can underlie the resistive heating element 16, with an overlayer 26 formed between the heat-spreading layer 28 and the heating element 16.

Figure 2E:
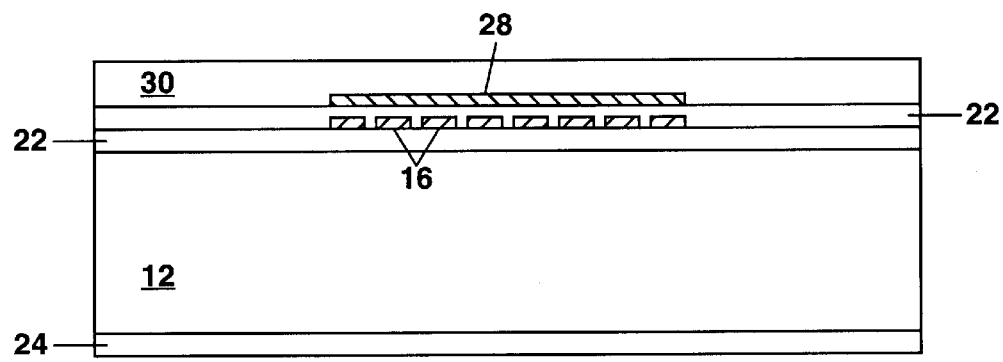

In FIG. 2e, a protection layer 30 is formed over the resistive heating element 16 and over the top surface of the substrate 12 to protect this side of the substrate 12 from exposure to a wet etchant during subsequent etching to remove material from the silicon substrate 12 and thereby form the suspended membrane 14. The protection layer 30 can comprise a layer of photoresist up to several microns thick which is spun on over the substrate and cured by baking. Later, the photoresist protection layer 30 can be removed using a solvent (e.g. acetone). Other types of materials can be used to form the protection layer 30 so long as the materials are chemically resistant to the etchant used to remove the silicon material and are subsequently removable without damaging the substrate 12, the heating element 16 or the membrane 14.

Figure 2F:
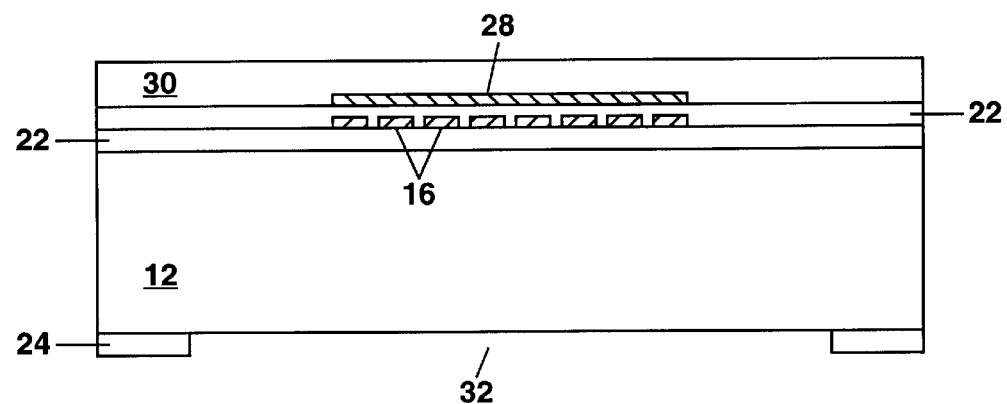

In FIG. 2f, an opening 32 is formed through the lower silicon nitride layer 24 to expose the bottom surface of the substrate 12. This can be done by using a doublesided photolithographic mask aligner to center the opening 32 to be formed in the layer 24 with the resistive heating element 16. To form the opening 32, a mask comprising photoresist or silicon dioxide can be formed on the bottom surface of the substrate 12 and used to etch through the lower silicon nitride layer 24 by either wet etching or preferably by anisotropic dry etching (e.g. reactive ion etching). The mask (not shown) can be left in place during subsequent etching of the substrate 12. In the case of etching the substrate 12 with potassium hydroxide (KOH), a thick (e.g. 0.5–1 $\mu$m) silicon dioxide or LPCVD silicon nitride mask is preferred as being more robust than a photoresist mask.

Figure 2G:
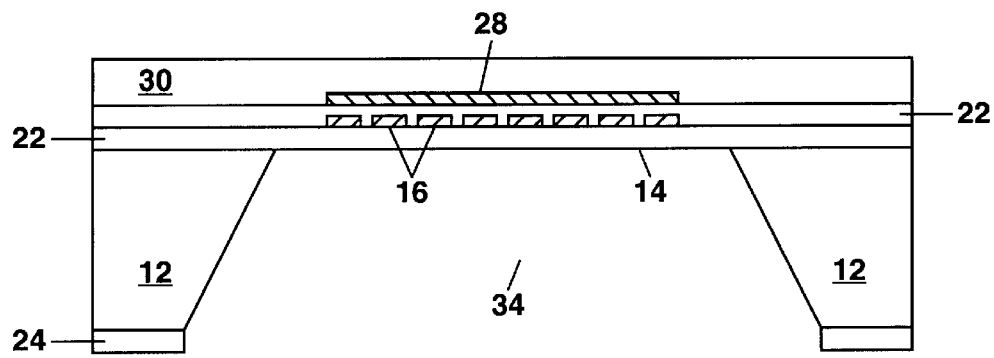

In FIG. 2g, the silicon substrate 12 can be etched from the bottom surface (i.e. from the backside of the substrate 12) to remove material from the substrate 12 at the location where the suspended membrane 14 is to be formed. To etch away the silicon, an anisotropic wet etchant comprising potassium hydroxide (KOH), tetramethyl ammonium hydroxide (TMAH) or ethylenediamine pyrocatechol (EDP) can be used. These etchants are selective in that they terminate upon reaching (111) crystallographic planes in silicon, and upon reaching the upper silicon nitride layer 22 which acts as an etch stop. The result is that the silicon is removed from the substrate 12 to form a cavity 34 having angled sidewalls, thereby producing the suspended membrane 14 from the upper silicon nitride layer 22. In other embodiments of the present invention, a (110)-oriented silicon substrate 12 can be used to provide (111) crystallographic planes that are aligned substantially perpendicular to the surfaces of the substrate 12 so that vertical sidewalls are formed.

Figure 2H:
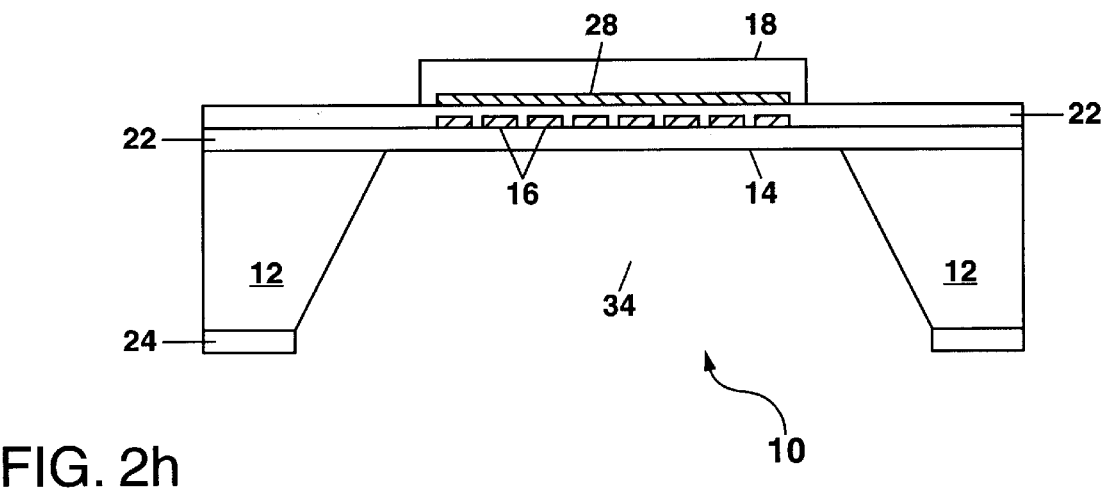

In FIG. 2h, the protection layer 30 is removed from the substrate 12; and a coating of a sorptive material 18 is deposited over the resistive heating element 16 and patterned to conform substantially to the outline of the heating element 16. The sorptive material 18, which preferably has a layer thickness ranging from about 1 $\mu$m to several $\mu$m and can be formed from one or more layers, comprises a material that selectively sorbs one or more chemical species of interest while preferably not substantially sorbing other chemical species which are not of interest (e.g. constituents of the atmosphere such as water vapor or methane, or interfering chemical species present in an ambient or a sample vapor). Suitable sorptive materials include polymers (e.g. styrene divinyl benzene), many different types of microporous materials such as porous polymers, porous silicon, porous metals (e.g. platinum), porous carbon and porous oxides (e.g. sol-gel oxides).

Chemically-selective sorptive coatings are well-known in the art and have been previously used, for example, to selectively sorb particular chemical species on acoustic wave sensors for detection by mass loading although such chemically-selective coatings to our knowledge have not previously been formed on a suspended membrane having an integral heating element. See, for example, an article by M. S. Nieuwenhuizen et al entitled "Surface Acoustic Wave Chemical Sensors," in *Sensors and Materials*, vol. 5, pp. 261–300, 1989 which discloses different types of polymers which can be prepared to selectively sorb particular chemical species, including polymers which selective sorb a nerve agent simulant dimethyl methyl phosphonate (DMMP). The preparation of surfactant-templated microporous oxides (including silicon dioxide which is also termed silica) based on sol-gel oxides which are preferred for use as the sorptive material 18 have been disclosed in an article by N. K. Raman et al entitled "Template-Based Approaches to the Preparation of Amorphous, Nanoporous Silicas," in *Chemistry of*

*Materials*, vol. 8, pp. 1682–1701, 1996; and in another article by Y. Lu et al entitled "Microporous Silica Prepared by Organic Templating: Relationship Between the Molecular Template and Pore Size," in *Chemistry of Materials*, vol. 11, pp. 1223–1229, April 1999. The preparation of other microporous sol-gel oxides are disclosed in an article by G. C. Frye et al entitled "Controlled Microstructure Oxide Coatings for Chemical Sensors," in *Proceedings of the 1990 Solid State Sensors and Actuators Workshop*, pp. 61–64, IEEE, New York, 1990; in U.S. Pat. Nos. 5,224,972 and 5,589,396 to Frye et al; and in U.S. Pat. No. 5,770,275 to Raman et al. Each of the above articles and patents are incorporated herein by reference.

The ability of the sorptive material 18 to sorb particular chemical species of interest can be based on chemical selectivity, or steric selectivity, or both. Chemical selectivity can be provided in several ways: by surface modification, by novel composition coatings, or by entrapped chemicals which act to bind the chemical species of interest while not substantially binding other chemical species which are not of interest. Steric selectivity can be provided by tailoring the porosity and pore size distribution of the sorptive material 18 to allow the chemical species of interest to be trapped within active sites in pores of the sorptive material 18 while excluding unwanted chemical species from the active sites based on steric constraints (i.e. molecules too large to fit within the pores of the sorptive material 18).

In FIG. 2h, various methods can be used to deposit the sorptive material 18, including dip-coating, spin-coating, spraying, electrospraying, and inkjet deposition. For example, the sorptive material 18 (e.g. a microporous hydrophobic sol-gel) can be sprayed onto the substrate 12 through a contact mask or through a shadow mask (not shown). If heat curing of the sorptive material 18 is necessary, this can be performed (e.g. at about 400° C.) either in an oven, or alternately in situ by using the resistive heating element 16. In situ curing of the deposited sorptive material 18 by applying electrical power to the resistive heating element 16 can be advantageous since any unheated and uncured portions of the sorptive material 18 can be removed by rinsing them away using a solvent (e.g. ethanol). This also precisely matches the size of the cured sorptive material 18 to that of the resistive heating element 16.

FIGS. 3a–3e show an alternate method for forming the chemical preconcentrator 10 of the present invention which can be preferred when space on the substrate 12 is at a premium (e.g. to reserve space for other elements such as integrated circuitry and/or a gas chromatographic channel and detector on the substrate 12 proximate to the chemical preconcentrator 10). This second method for forming the chemical preconcentrator 10 of the present invention will be described in terms of forming a device 10 on a silicon substrate 12 without a heat-spreading layer 28.

The initial steps to fabricate the chemical preconcentrator 10 according to this second method can proceed as shown and described with reference to FIGS. 2a and 2b.

Figure 3A:
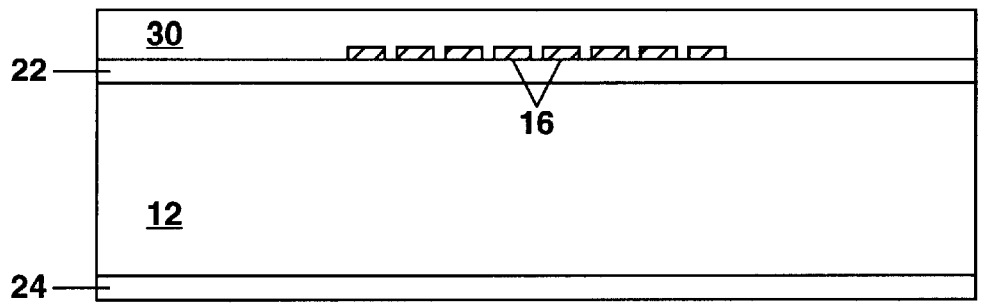
FIGS. 3a–3e show schematic cross-section views to illustrate a second method for forming the chemical preconcentrator.

In FIG. 3a, after formation of the resistive heating element 16 as described previously, a protection layer 30 (e.g. 0.5–5 $\mu$m of photoresist) can be formed over the top surface of the substrate 12 and the heating element 16 for protection during etching of the substrate 12 from its backside. This can be done as described previously with reference to FIG. 2e.

Figure 3B:
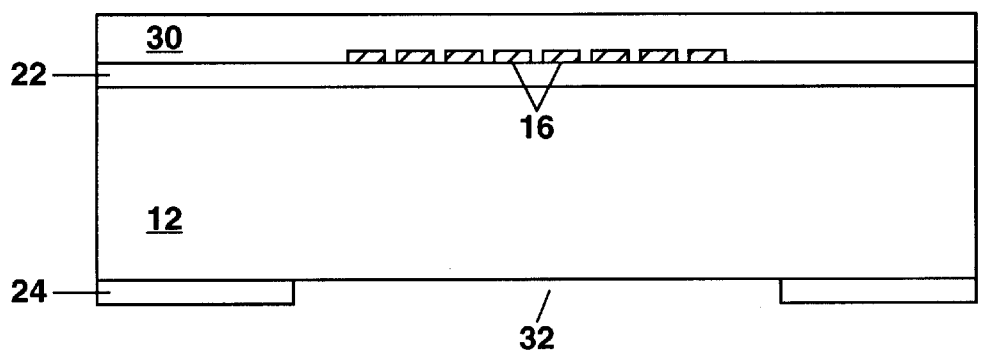

In FIG. 3b, an opening 32 can be formed through the lower silicon nitride layer 24 to expose the bottom surface of the substrate 12 as described previously with reference to FIG. 2f.

Figure 3C:
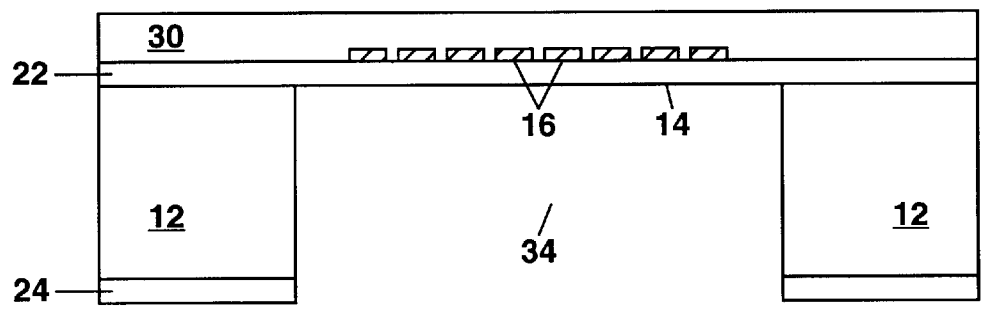

In FIG. 3c, a cavity 34 can be etched through the thickness of the substrate 12 using an anisotropic dry etching process, with the patterned lower silicon nitride layer 24 and an overlying photoresist mask (not shown) serving as the etch mask. A preferred process for performing this dry etching through the substrate 12 is to use a deep reactive ion etching process which minimizes lateral etching. Such a deep reactive ion etching process is disclosed, for example, in U.S. Pat. No. 5,501,893 to Laermer et al, which is incorporated herein by reference. The deep reactive ion etching process of Laermer et al, which is termed the Bosch process or alternately the High Aspect Ratio Silicon Etching (HARSE) process, is based on alternating etching steps and polymer formation steps. Initially, the substrate 12 is partially etched from the backside for a few microns by exposure to an $SF_6$/Ar plasma in a reactive ion etching system. Then the etched sidewalls are covered with a deposited isotropic polymer/inhibitor by providing one or more polymer-formers (e.g. $CHF_3$ and Ar) to the plasma. The deposited polymer/inhibitor acts as an etch stop to prevent lateral etching of the sidewalls during a subsequent etching step. This process of alternating etching steps (i.e. etching for a few microns) and polymer formation steps is repeated numerous times until the cavity 34 is formed through the substrate 12 to expose the upper silicon nitride layer 22 as shown in FIG. 3c.

The use of anisotropic dry etching to form the cavity 34 as described above can be advantageous since the Bosch etch rate for silicon is about 3 $\mu$m/minute or more, which is at least twice the etch rate using KOH. Additionally, a photoresist mask can be used in combination with the patterned lower silicon nitride layer 24 or in place of the layer 24 when using the Bosch process; whereas other etching processes may require the use of a hard mask (e.g. comprising nickel). The use of a photoresist mask saves time compared to the formation of a thick (0.5–1 $\mu$m) silicon dioxide mask which can require up to several hours. In the event that there is some silicon remaining below the membrane 14 near the sidewalls of the cavity 34 forming a "foot" after the Bosch process, the remaining silicon can be removed by an anisotropic wet etchant step (e.g. using KOH).

Figure 3D:
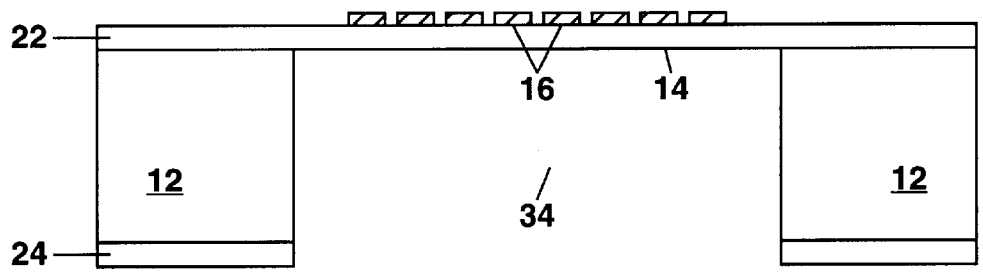
Figure 3E:
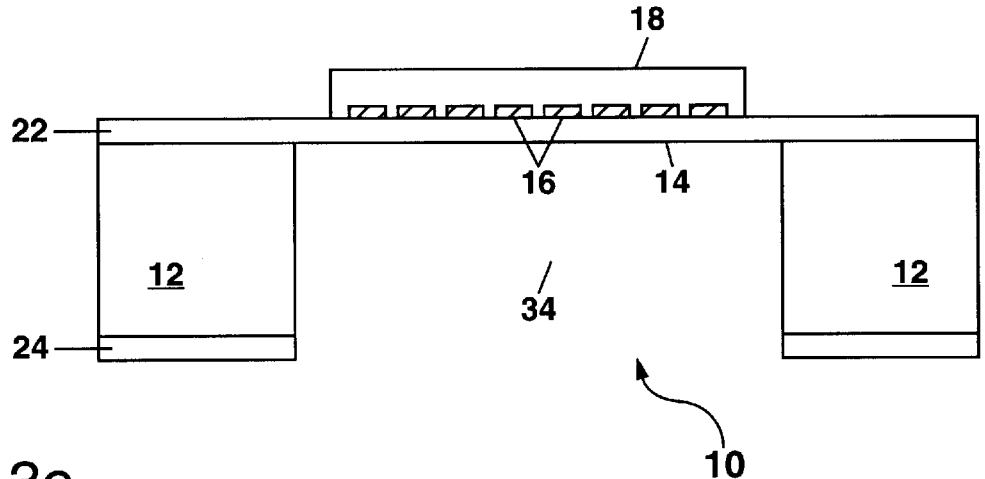

In FIG. 3d, the protection layer 30 is removed (e.g. by dissolving a layer 30 of photoresist in acetone or in a commercial photoresist stripping solution). In FIG. 3e, the sorptive material 18 can then be formed over the resistive heating element 16 as described previously with reference to FIG. 2h.

A third method for forming the chemical preconcentrator 10 is described with reference to FIGS. 4a–4f, and uses conventional surface micromachining processes. Surface micromachining is based on the deposition and patterning of alternating layers of a sacrificial material and a structural material on a substrate 12. The sacrificial material is then removed to leave the structural material which forms the completed device. On a silicon substrate 12, polycrystalline silicon (also termed polysilicon) is generally used as the structural material, with the sacrificial material generally being silicon dioxide or a silicate glass. The silicate glass can be formed, for example, from the decomposition of tetra-ethylortho silicate (TEOS), and densified by heating to a high temperature. On an oxide-based substrate (e.g. glass, fused silica, crystalline quartz, or ceramic), polysilicon can be used as the sacrificial material, with silicon dioxide or a silicate glass being used as the structural material. The sacrificial material can also comprise a polymer (e.g. photoresist) which can be used with any of the above types of substrates and also including polymer substrates (i.e. comprising polymers other than photoresist) or resin substrates. When photoresist is used as a sacrificial material, it can be subsequently removed by solvent dissolution (e.g. with acetone, or with a commercial photoresist stripper).

Figure 4A:
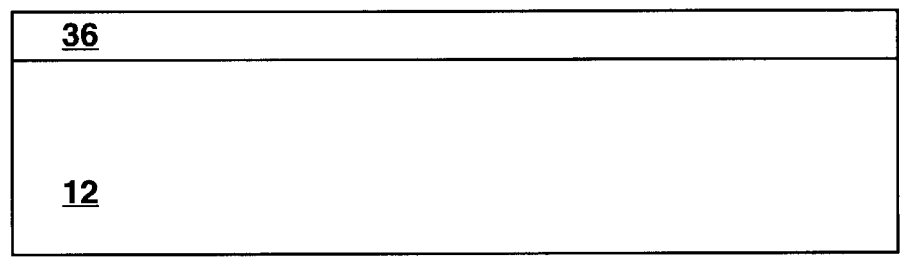
FIGS. 4a–4f show schematic cross-section views to illustrate a third method for forming the chemical preconcentrator.

In FIG. 4a, a substrate 12 is provided and a sacrificial layer 36 is formed over the top surface of the substrate 12, with the sacrificial layer 36 being, for example, 1–5 $\mu$m thick. The particular material used for the sacrificial layer 36 will depend on various factors including the composition of the substrate 12, the temperature at which subsequent layers (e.g. for forming the membrane 14 and the heating element 16) must be deposited, and on whether the sacrificial layer 36 is to be removed, at least in part, by selective wet etching or by solvent dissolution. Silicon dioxide or a silicate glass (e.g. TEOS) can be used to form the sacrificial layer 36 when the substrate 12 comprises silicon and when subsequent depositions must be performed at temperatures up to several hundred ° C. Polysilicon can be used as the sacrificial layer 36 when the substrate comprises a glass, ceramic, fused silica or crystalline quartz, and when subsequent depositions are at temperatures up to several hundred ° C. A polymer (e.g. photoresist) can be used for the sacrificial layer 36 when subsequent deposition occurs at a relatively low temperature of about 100° C. or less (e.g. with a silicon oxynitride membrane 14 deposited near room temperature).

Figure 4B:
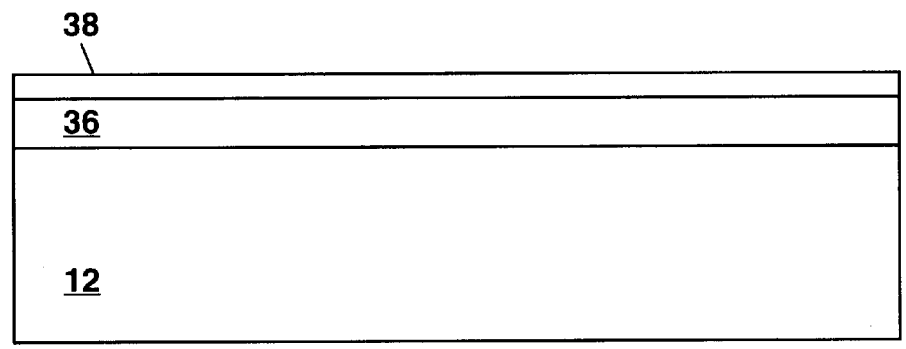

In FIG. 4b, a membrane-forming film 38 with a thickness of about 1 $\mu$m is deposited over the sacrificial layer 36. Depending upon the composition of the sacrificial layer 36 and the substrate 12, the membrane-forming film 38 can comprise silicon nitride, silicon (e.g. polycrystalline silicon), silicon oxynitride or silicon carbide. For example, on a silicon substrate 12 with a silicon dioxide or sacrificial glass layer 36, the membrane-forming film 38 can comprise silicon nitride, or alternately polysilicon. As another example, on a silicon substrate 12 having a photoresist sacrificial layer 36, the membrane-forming film 38 can comprise silicon oxynitride ($SiO_xN_y$) deposited at a relatively low temperature (i.e. $\leq 100°$ C.) using a high-density plasma (e.g. an electron-cyclotron resonance plasma) and with a composition selected to provide a low residual stress.

Figure 4C:
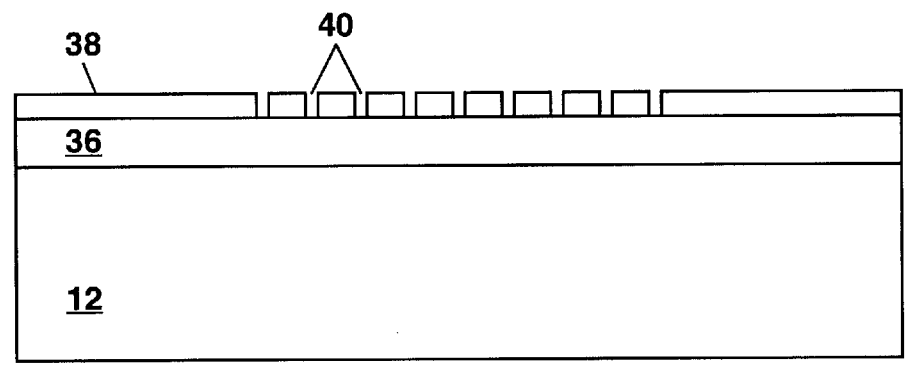

In FIG. 4c, a plurality of shaped openings 40 can be formed downward through the membrane-forming film 38 to expose the underlying sacrificial layer 36. This can be done, for example, by forming a patterned etch mask (not shown) over the film 38 and then anisotropically dry etching through the film 38 (e.g. using reactive ion etching) to form the shaped openings 40. The shaped openings 40 can be formed, for example, as an array of openings having micron-sized dimensions or larger, or alternately as an array of channels or slots. The openings 40 can be located interspersed between a plurality of longitudinal segments of the circuitous metal trace, formed outside the circuitous metal trace, or both.

Figure 4D:
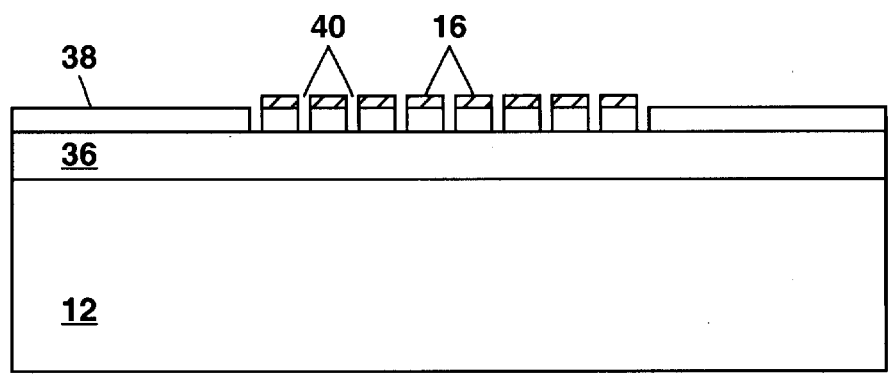

In FIG. 4d, the resistive heating element 16 is formed over the membrane-forming film 38. This can be done as previously described with reference to FIG. 2b. In some embodiments of the present invention, the steps in FIGS. 4c and 4d can be reversed.

Figure 4E:
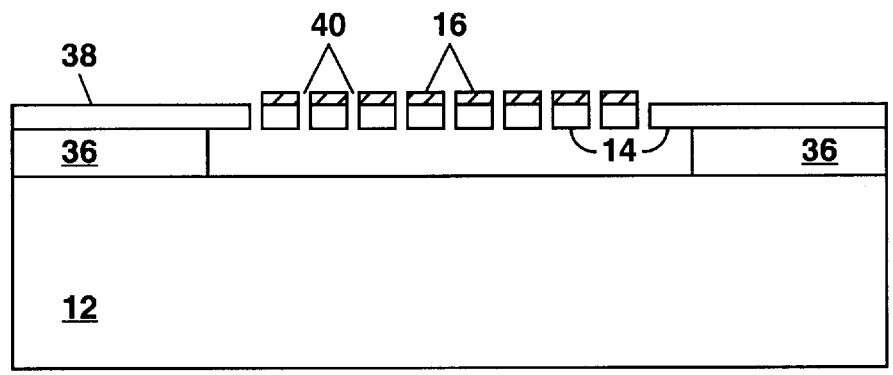

In FIG. 4e, the sacrificial layer 36 can be partially removed by etching downward through each shaped opening 40 and laterally outward from each opening 40. This can be done using a selective wet etchant comprising HF for a sacrificial layer 36 comprising silicon dioxide or silicate glass, or alternately using a solvent for a polymer sacrificial layer 36. The etching or solvent dissolution step can be timed so that only material in the sacrificial layer 36 within a predetermined distance from the shaped openings 40 is removed, with the remainder of the sacrificial layer 36 serving as a support for the suspended membrane 14 formed in this step. During removal of a part of the sacrificial layer 36 underlying the resistive heating element 16 and membrane-forming layer 38, a protection layer 30 can optionally be provided over these layers and patterned to provide access to the openings 40. However, when the resistive heating element 16 comprises metals that are resistant to attack by the selective wet etchant (e.g. titanium, tungsten, platinum and gold for an etchant comprising HF) used to remove a part of the sacrificial layer 36, no protection layer 30 is generally needed. Similarly, no protection layer 30 is generally needed when solvent dissolution is used to remove a part of a photoresist sacrificial layer 36.

Figure 4F:
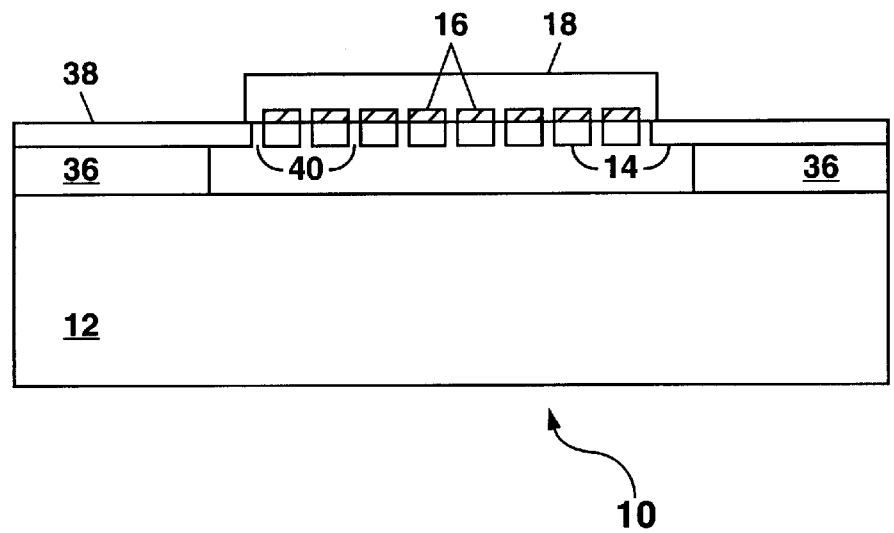

In FIG. 4f, a layer of a sorptive material 18 up to several microns thick is deposited over the resistive heating element 16 as described previously with reference to FIG. 2h. The layer of sorptive material 18, which can overlie the plurality of shaped openings 40 as shown in FIG. 4f, will generally have a sufficiently high viscosity so that the sorptive material 18 does not penetrate completely through the openings 40. Alternately, deposited material (e.g. PECVD silicon nitride) can be used to fill in the openings 40 prior to deposition of the sorptive material 18.

Figure 5:
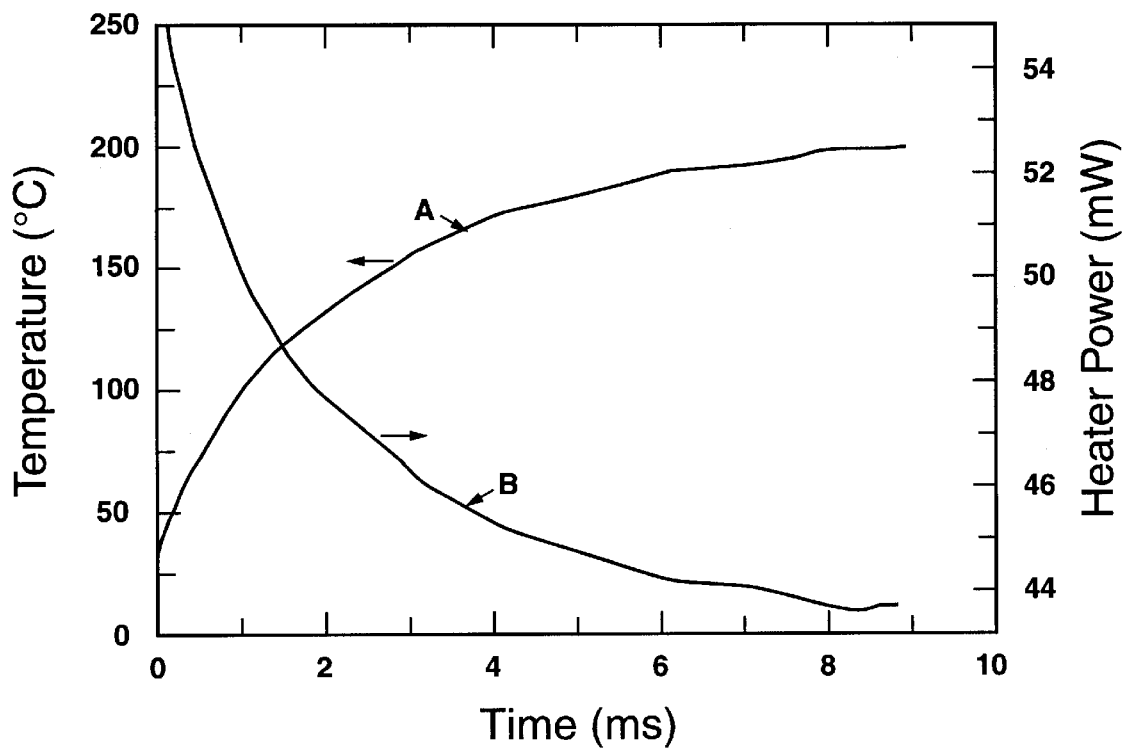
FIG. 5 shows test data for the heating performance of a chemical preconcentrator formed according to the present invention.

FIG. 5 shows test data for the heating performance of a chemical preconcentrator 10 formed according to the present invention with a 2-mm-square x 0.5-$\mu$m-thick silicon nitride membrane 14 and with a resistive heating element 16 comprising titanium and platinum. No coating of sorptive material 18 was present on the membrane 14 for these tests; but the addition of a coating of sorptive material 18 is not expected to substantially change the curves from those shown in FIG. 5. The chemical preconcentrator 10 can be heated to a typical desorption temperature of about 200° C. in 6–8 milliseconds as shown in the curve in FIG. 5 labelled "A". The temperature was measured by monitoring the resistance of the heating element 16 (i.e. by measuring the voltage and current supplied to the heating element 16), thereby using the heating element itself as a resistance temperature sensor or in a feedback loop for temperature control of the heating element 16.

In other embodiments of the present invention, a temperature sensor in the form of a resistance temperature sensor (e.g. comprising platinum) or a thermocouple temperature sensor can be provided on the membrane 14 proximate to the heating element 16. In the example of FIG. 1a, such a temperature sensor or thermocouple could be located on the membrane 14 between the two resistive heating elements 16 or to the side of one of the heating elements 16. In these embodiments of the present invention employing a separate temperature sensor, the temperature sensor can also be used in a feedback loop to control and measure the temperature to which the sorptive material 18 is heated.

The curve labelled "B" in FIG. 5 shows the electrical power supplied to the resistive heating element 16 for heating of the chemical preconcentrator 10. Once this chemical preconcentrator 10 was heated to a desorption temperature of 200° C., it could be maintained at this temperature for sufficient time to completely desorb the chemical species of interest using an electrical input power of less than 50 milliwatts.

In another test, a chemical preconcentrator 10 having a 2.4-mm-diameter circular membrane 14 was heated to a temperature of 400° C. in 15 milliseconds and maintained at that temperature with an electrical input power of 220 milliwatts. The chemical preconcentrators 10 of the present invention without an aluminum heat-spreading layer 28 are expected to be operable at temperatures up to about 700° C.

Figure 6:
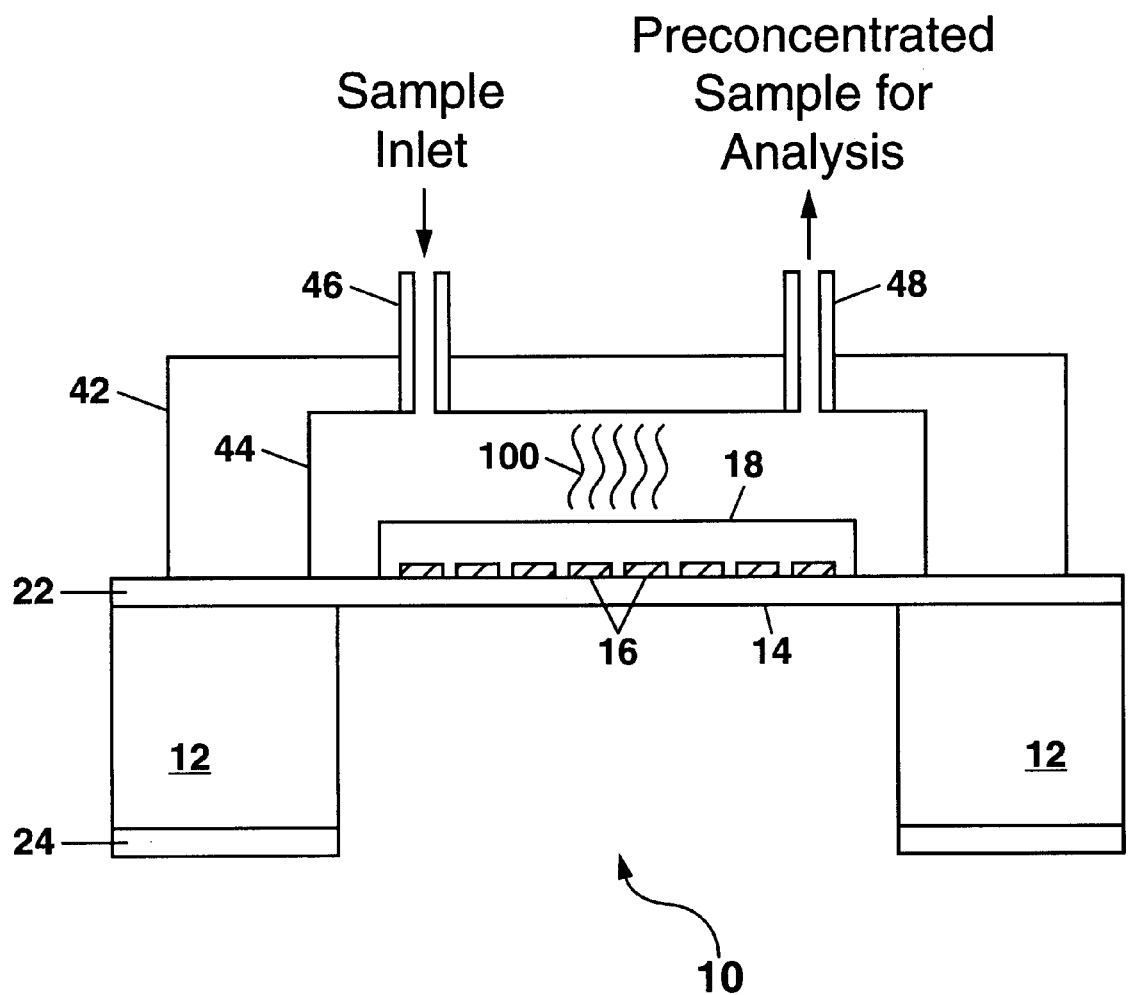
FIG. 6 schematically illustrates in cross-section view a chemical preconcentrator apparatus fixtured for testing with a sample vapor.

To test operation of the chemical preconcentrator 10 with a chemical species of interest, the apparatus 10 was fixtured as shown in FIG. 6 with an attached glass lid 42 having an etched flow channel 44 and a plurality of capillary tubes, including an inlet capillary tube 46 for admitting a sample vapor 100 and an outlet capillary tube 48 for providing the preconcentrated sample containing the chemical species of interest to a flame ionization detector (not shown). The sample vapor 100, which comprised a mixture of 5 parts-per-million (ppm) of DMMP in air, was supplied to the preconcentrator 10 via the sample inlet 46 over a time duration of one minute, with the DMMP being sorbed onto a microporous hydrophobic sol-gel sorptive material 18. The chemical preconcentrator 10 was then rapidly heated to a temperature of 200° C. by the application of a square voltage pulse of about one second duration to the resistive heating element 16. This released the preconcentrated DMMP for detection in a concentrated sample plug having a time duration of about 200 milliseconds full-width at half-maximum.

Figure 7:
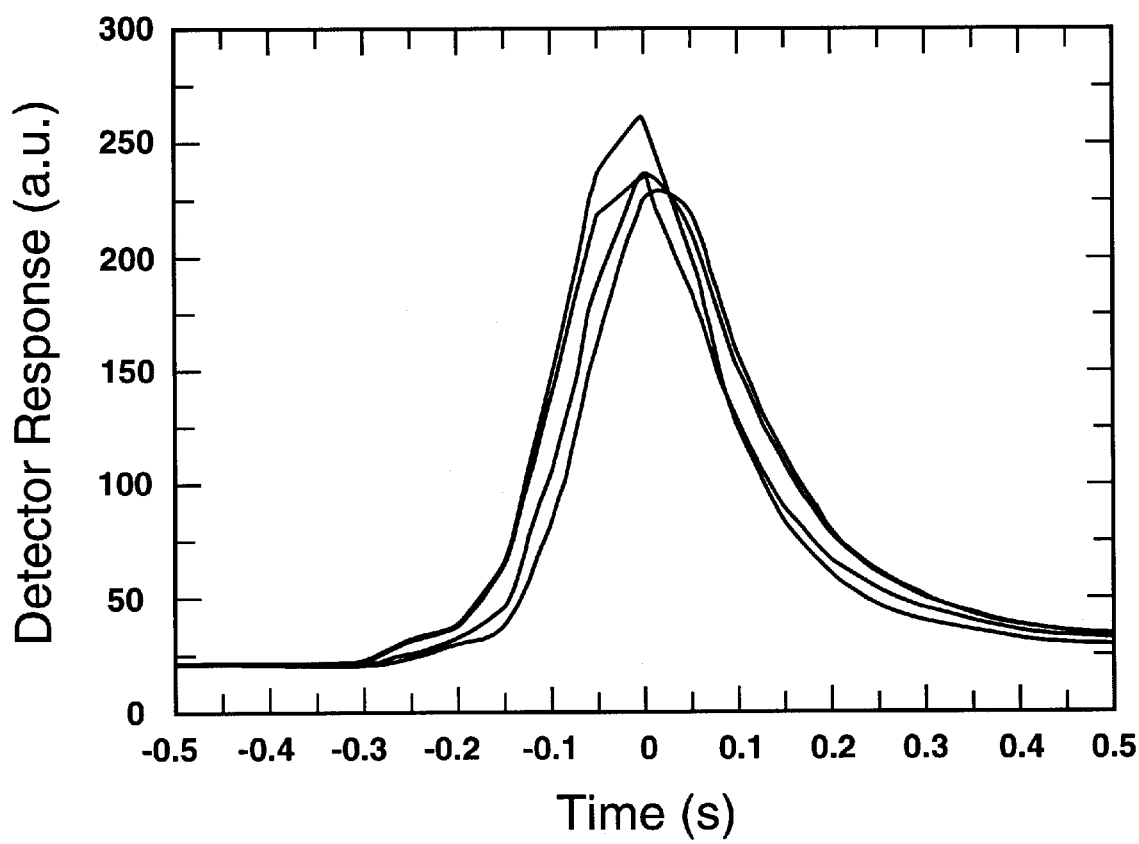
FIG. 7 shows a series of thermal desorption response curves to illustrate the reproducibility which can be achieved with a chemical preconcentrator of the present invention for sorbing and releasing a particular chemical species.

To measure the reproducibility with which the DMMP sample can be accumulated and released for measurement, the chemical preconcentrator apparatus 10 was repeatedly cycled for four times. The resultant flame ionization detector response curves are overlaid in FIG. 7 to show the good reproducibility of the chemical preconcentrator 10 and lack of any appreciable memory effect.

Figure 8:
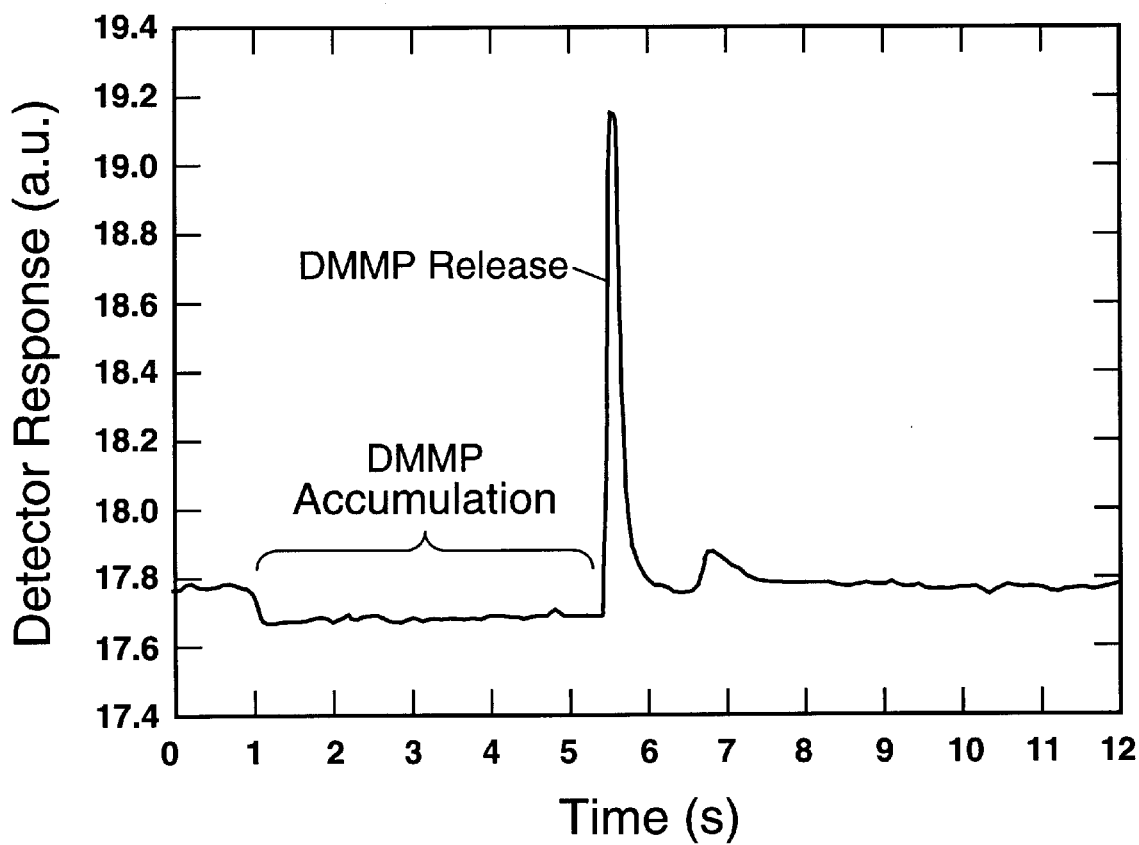
FIG. 8 shows a thermal desorption response curve for the chemical preconcentrator to illustrate sorption of a chemical species of interest over a period of time and subsequently releasing the chemical species upon heating to form a concentrated sample plug having a narrow temporal width for analysis.

FIG. 8 shows results obtained using the same chemical preconcentrator 10 with the concentration of DMMP in air reduced to 50 parts-per-billion (ppb). Here, the chemical preconcentrator 10 was loaded for about 4 seconds to selectively sorb the DMMP Then the preconcentrator 10 was heated to 200° C. with a voltage pulse to suddenly release the sorbed DMMP in a fraction of a second as a concentrated sample plug having a narrow temporal width for detection using the flame ionization detector. The result is that the 50 ppb level of DMMP could easily be detected above the detector background signal in a time period of only 5 seconds.

The chemical preconcentrator 10 of the present invention has applications for use with different chemical analysis methods including chromatography and mass spectrometry. In a gas chromatograph, the differentiation between chemical species in a sample is achieved via their differential migration through a capillary column. A sample vapor is injected at the input of the column and is swept through the column by an inert carrier gas (e.g. helium or argon). The column is lined with a liquid stationary phase material, a substance capable of sorbing and desorbing each of the component chemical species in the sample vapor. The migration rate of each chemical species along the column depends on the carrier gas velocity and the degree to which that chemical species is sorbed by the stationary phase material. The sample vapor, injected into the column as a single pulse (i.e. a sample plug), is separated as it travels through the column, with each component chemical species traveling at a different rate and emerging at a specific time for detection. The column's output is thus a series of peaks corresponding to the different chemical species in the sample vapor separated in time by regions of pure carrier gas. Resolution is enhanced by providing the sample vapor as a narrow-temporal-width pulse (i.e. the narrower the temporal width of the sample plug, the better the chromatography). To detect these peaks, an output gas stream from the column containing the different chemical species and the carrier gas is passed over a detector which measures a particular property of the gas to generate an output signal which can be recorded over time to indicate the presence and quantity of the different chemical species in the vapor sample from each species retention time in the column and the area under its output peak. Suitable detectors can be flame ionization detectors, thermal conductivity detectors, acoustic wave devices (e.g. surface acoustic wave devices, or flexural plate wave devices), etc.

In gas chromatography, the sensitivity and selectivity can be improved by preconcentrating the sample vapor into a sample plug having a narrow temporal width and a relatively high concentration of the chemical species of interest. This can be done using the chemical preconcentrator 10 of the present invention as a front end to a gas chromatography system. By accumulating the chemical species of interest from an ambient or a sample vapor 100 and then releasing the accumulated chemical species of interest as a sample plug with a narrow temporal width, peak spreading within the flow column can be minimized. This facilitates the separation of a plurality of different chemical species from the ambient or sample vapor 100 while at the same time maximizing the peak height for particular chemical species of interest. As a result, the signal-to-noise ratio at the detector is increased compared to an analytical measurement performed without the preconcentrator 10. Additionally, since the chemical preconcentrator 10 can be made selective for particular chemical species of interest thereby producing a sample plug which is relatively free of potentially interfering chemical species, its addition to a gas chromatography system can further improve the selectivity and sensitivity of that system.

The chemical preconcentrator 10 of the present invention can be integrated with a gas chromatography column and with a detector in a hybrid or monolithic fashion to provide, for example, a compact hand-held, battery-powered analytical instrument for rapid and sensitive analysis of one or more chemical species of interest (e.g. pollutants, high explosive vapors or nerve gas agents). In a hybrid gas chromatograph, the chemical preconcentrator 10 can be attached or bonded to a separate substrate in which the gas chromatograph column is formed and connected to one end of the column. A hybrid or monolithic detector can be provided at the other end of the column. In a monolithic gas chromatograph, the chemical preconcentrator 10, the gas chromatograph column, and the detector can all be formed on or within a single substrate 12 (e.g. comprising silicon) and interconnected by channels etched into the substrate 12 (e.g. using the Bosch process). This has an advantage of minimizing a transfer path length between the various elements of the gas chromatograph thereby minimizing sample loss and degradation which can otherwise reduce the sample concentration in the sample plug and broaden its temporal width, thereby degrading measurement resolution of the gas chromatograph.

Similarly, the chemical preconcentrator 10 can be used in a mass spectrometry system which separates different chemical species according to their mass (or the mass of fragments from each chemical species). The preconcentrator 10 can improve the sensitivity and selectivity for mass spectrometry by sorbing and concentrating particular chemical species of interest from a sample vapor 100, while sorbing little, if any, of particular interferent chemical species which are not of interest.

In other embodiments of the present invention, the resistive heating element 16 can be used to dry a liquid sample placed on the sorptive material 18 prior to analysis of the sample. Drying of the sample can be performed by heating the sorptive material 18 to a temperature slightly lower than the boiling point of the sample. Once the sample is dried and the chemical species of interest are concentrated, the heating element 16 can be heated to a temperature sufficiently high to desorb the chemical species of interest for subsequent analysis with a gas chromatograph or a mass spectrometer.

The matter set forth in the foregoing description and accompanying drawings is offered by way of illustration only and not as a limitation. Other applications and variations of the present invention will become evident to those skilled in the art. For example, in some embodiments of the present invention, a composite membrane 14 can be used to reduce intrinsic stress in the membrane 14. Such a composite membrane 14 can comprise, for example, a pair of tensile-stressed layers of plasma-enhanced chemical vapor deposited (PECVD) silicon nitride (e.g. about 0.1 $\mu$m thick) sandwiched about a compressively-stressed layer of PECVD silicon dioxide (e.g. about 0.5 $\mu$m thick). In other embodiments of the present invention, the coating of sorptive material 18 can be applied to a lower surface of the membrane 14, or on both surfaces of the membrane 14. The chemical preconcentrator 10 of the present invention can be used with other types of detectors as known to the art, and in other types of chemical sensing systems, including electrochemical sensors, acoustic-wave sensors, and ion mobility spectrometers. The actual scope of the invention is intended to be defined in the following claims when viewed in their proper perspective based on the prior art.

What is claimed is:

1. A chemical preconcentrator apparatus, comprising:
    (a) a substrate having a suspended membrane formed thereon;
    (b) a resistive heating element disposed on a surface of the membrane; and
    (c) a sorptive material disposed on at least one surface of the membrane to sorb and concentrate at least one chemical species of interest from a vapor over time, with the chemical species being releasable from the sorptive material upon heating of the sorptive material by the resistive heating element.

2. The apparatus of claim 1 wherein the substrate is selected from the group consisting of semiconductors and dielectrics.

3. The apparatus of claim 2 wherein the substrate comprises silicon.

4. The apparatus of claim 1 wherein the membrane comprises a material selected from the group consisting of silicon nitride, polycrystalline silicon, silicon oxynitride and silicon carbide.

5. The apparatus of claim 1 wherein the resistive heating element comprises a circuitous metal trace.

6. The apparatus of claim 5 wherein the metal comprises a metal selected from the group consisting of platinum, molybdenum, titanium, chromium, palladium, gold, tungsten and combinations thereof.

7. The apparatus of claim 5 further including a heat-spreading layer disposed over the resistive heating element to provide a more uniform heating of the sorptive material.

8. The apparatus of claim 7 wherein the heat-spreading layer comprises aluminum or silicon.

9. The apparatus of claim 1 wherein the sorptive material comprises a microporous material.

10. The apparatus of claim 1 wherein the sorptive material comprises a sol-gel oxide.

11. The apparatus of claim 10 wherein a surface of the sol-gel oxide is chemically modified to enhance sorption of the chemical species of interest.

12. The apparatus of claim 1 wherein the sorptive material comprises a polymer.

13. A method for forming a chemical preconcentrator apparatus for sorbing a chemical species of interest from a vapor over time and releasing the chemical species of interest upon demand, comprising steps for:
    (a) forming a suspended membrane on a substrate;
    (b) forming a resistive heating element on a surface of the suspended membrane; and
    (c) coating at least one surface of the suspended membrane with a sorptive material capable of sorbing the chemical species of interest.

14. The method of claim 13 wherein the suspended membrane comprises a material selected from the group consisting of silicon nitride, polycrystalline silicon, silicon oxynitride and silicon carbide.

15. The method of claim 13 wherein the step for forming the suspended membrane comprises steps for depositing a film over a top surface of the substrate, and removing material from the substrate underneath a portion of the deposited film.

16. The method of claim 15 wherein the step for removing material from the substrate underneath the portion of the deposited film comprises at least one step for etching the substrate from a surface thereof.

17. The method of claim 16 wherein the step for etching the substrate from the surface thereof comprises etching the substrate using an etching method selected from the group of etching methods consisting of anisotropic wet etching, reactive ion etching, and combinations thereof.

18. The method of claim 16 wherein the surface is a bottom surface, and the step for etching the substrate comprises etching through a majority of the thickness of the substrate using reactive ion etching, and etching through the remainder of the thickness of the substrate using anisotropic wet etching.

19. The method of claim 13 wherein the step for forming the suspended membrane comprises steps for:
    depositing a sacrificial layer over the substrate;
    depositing a film over the sacrificial layer;
    forming a plurality of openings through the film to expose the sacrificial layer; and
    removing, at least in part, the sacrificial layer through the openings formed in the film.

20. The method of claim 19 wherein the film is selected from the group consisting of silicon nitride, polycrystalline silicon, silicon oxynitride and silicon carbide; and the sacrificial layer is selected from the group consisting of silicon dioxide, silicate glasses and polymers.

21. The method of claim 20 wherein the step for removing the portion of the sacrificial layer comprises etching the sacrificial layer with a wet etchant comprising hydrofluoric acid.

22. The method of claim 20 wherein the step for removing the portion of the sacrificial layer comprises dissolving the sacrificial layer using a solvent.

23. The method of claim 13 wherein the step for forming the resistive heating element comprises depositing a metal layer and patterning the metal layer to form a circuitous metal trace.

24. The method of claim 23 wherein the metal layer comprises a metal selected from the group consisting of platinum, molybdenum, titanium, chromium, palladium, gold, tungsten and combinations thereof.

25. The method of claim 23 further including a step for annealing the circuitous metal trace for relieving any stress therein.

26. The method of claim 13 wherein the step for coating the surface of the suspended membrane comprises depositing a sorptive material selected from the group consisting of polymers, microporous materials, and sol-gel oxides.

27. The method of claim 26 further including a step for curing the deposited sorptive material by heating.

28. A method for forming a chemical preconcentrator apparatus for sorbing a chemical species of interest from a vapor over time and releasing the chemical species of interest upon demand, comprising steps for:

(a) depositing a film over a top surface of a substrate;

(b) forming a resistive heating element on a portion of the film;

(c) removing material from the substrate underneath the portion of the film and thereby forming a suspended membrane from the film; and (d) coating at least one surface of the suspended membrane with a sorptive material capable of sorbing the chemical species of interest.

29. The method of claim 28 wherein the film comprises a material selected from the group consisting of silicon nitride, polycrystalline silicon, silicon oxynitride and silicon carbide.

30. The method of claim 28 wherein the step for removing material from the substrate comprises a step for etching the substrate.

31. The method of claim 30 wherein the step for etching the substrate comprises etching the substrate using an etching method selected from the group of etching methods consisting of anisotropic wet etching, reactive ion etching, and combinations thereof.

32. The method of claim 30 wherein the step for etching the substrate comprises etching through the substrate from a bottom surface thereof.

33. The method of claim 32 wherein the step for etching the substrate from the bottom surface thereof comprises etching through a majority of the thickness of the substrate using reactive ion etching, and etching through the remainder of the thickness of the substrate using anisotropic wet etching.

34. The method of claim 28 wherein the step for forming the resistive heating element comprises depositing a metal layer and patterning the metal layer to form a circuitous metal trace.

35. The method of claim 34 wherein the metal layer comprises a metal selected from the group consisting of platinum, molybdenum, titanium, chromium, palladium, gold, tungsten and combinations thereof.

36. The method of claim 34 further including a step for annealing the circuitous metal trace for relieving any stress therein.

37. The method of claim 28 wherein the step for coating the surface of the suspended membrane comprises depositing a sorptive material selected from the group consisting of polymers, microporous materials, and sol-gel oxides.

38. The method of claim 37 further including a step for curing the deposited sorptive material by heating.

* * * * *